US011654426B2

(12) United States Patent
Matsukawa et al.

(10) Patent No.: US 11,654,426 B2
(45) Date of Patent: May 23, 2023

(54) METHOD FOR MANUFACTURING MODIFIED ALUMINOSILICATE, MODIFIED ALUMINOSILICATE, AND METHOD FOR MANUFACTURING AROMATIC DIHYDROXY COMPOUND USING THE SAME

(71) Applicant: MITSUI CHEMICALS, INC., Tokyo (JP)

(72) Inventors: Yoshiya Matsukawa, Iwakuni (JP); Nobuhiko Horiuchi, Chiba (JP); Akihiro Okabe, Narashino (JP); Yoshihiro Kubota, Yokohama (JP); Satoshi Inagaki, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 70 days.

(21) Appl. No.: 17/053,603

(22) PCT Filed: May 20, 2019

(86) PCT No.: PCT/JP2019/019939
§ 371 (c)(1),
(2) Date: Nov. 6, 2020

(87) PCT Pub. No.: WO2019/225549
PCT Pub. Date: Nov. 28, 2019

(65) Prior Publication Data
US 2021/0229085 A1    Jul. 29, 2021

(30) Foreign Application Priority Data
May 21, 2018 (JP) .............................. JP2018-097032
May 21, 2018 (JP) .............................. JP2018-097033

(51) Int. Cl.
*B01J 29/89*   (2006.01)
*B01J 37/08*   (2006.01)
*C01B 39/06*   (2006.01)
*C01B 39/48*   (2006.01)
*C07C 37/60*   (2006.01)
*C07C 39/08*   (2006.01)

(52) U.S. Cl.
CPC .............. *B01J 37/08* (2013.01); *B01J 29/89* (2013.01); *C01B 39/06* (2013.01); *C01B 39/48* (2013.01); *C07C 37/60* (2013.01); *C07C 39/08* (2013.01)

(58) Field of Classification Search
CPC ...... B01J 37/08; B01J 35/023; B01J 35/1038; B01J 35/1023; B01J 29/061; B01J 29/076; B01J 2229/16; C01P 2002/84; C07B 61/00; C07C 39/08; C07C 37/60; C01B 39/06; C01B 39/065; C01B 39/026; C01B 39/48

USPC ...................................................... 502/60, 73
See application file for complete search history.

(56) References Cited

U.S. PATENT DOCUMENTS

| | | | |
|---|---|---|---|
| 5,684,170 A | * | 11/1997 | Saxton ...................... B01J 29/89 |
| | | | 549/531 |
| 6,114,551 A | * | 9/2000 | Levin .................... C07D 301/19 |
| | | | 549/510 |
| 6,475,465 B2 | | 11/2002 | Lin et al. |
| 6,479,711 B1 | | 11/2002 | Takai et al. |
| 9,540,298 B2 | | 1/2017 | Goto et al. |
| 9,682,909 B2 | | 6/2017 | Corre et al. |
| 10,173,954 B2 | | 1/2019 | Corre et al. |
| 2001/0021369 A1 | | 9/2001 | Lin et al. |
| 2011/0034711 A1 | | 2/2011 | Kawabata et al. |
| 2015/0299076 A1 | | 10/2015 | Corre et al. |
| 2016/0176795 A1 | | 6/2016 | Goto et al. |
| 2017/0253547 A1 | | 9/2017 | Corre et al. |

FOREIGN PATENT DOCUMENTS

| | | |
|---|---|---|
| JP | 2001-206714 A | 7/2001 |
| JP | 2008-50186 A | 3/2008 |
| JP | 4254009 B2 | 4/2009 |
| JP | 2009-274062 A | 11/2009 |
| JP | 2015-511945 A | 4/2015 |
| JP | 2017-57126 A | 3/2017 |
| WO | 2015/041137 A1 | 3/2015 |
| WO | WO 2020/038222 * | 2/2020 |

OTHER PUBLICATIONS

Kraushaar et al., A New Method for the Preparation of Titanium-Silicalite (TS-1), Catalysis Letters, 1, 1988, pp. 81-84.*
Ziyath et al., "Influence of Physical and Chemical Parameters on the Treatment of Heavy Metals in Polluted Stormwater Using Zeolite—A Review", Journal of Water Resource and Protection, 2011, 3, pp. 758-767.*
Inagaki et al., "Enhancement of para-selectivity in the phenol oxidation with H2O2 over Ti-MCM-68 Zeolite catalyst", Green Chemistry, 2016, vol. 18, No. 3, pp. 735-741; Cited in ISR and Written Opinion of the International Searching Authority.
International Search Report (ISR) dated Aug. 20, 2019 filed in PCT/JP2019/019939.

(Continued)

*Primary Examiner* — Elizabeth D Wood
(74) *Attorney, Agent, or Firm* — Rankin, Hill & Clark LLP

(57) ABSTRACT

The method for manufacturing a modified aluminosilicate includes a first step of treating an aluminosilicate with an acid, a second step of primarily calcining the treated material obtained in the first step at 550° C. to 850° C., and a third step of contacting the calcined material obtained in the second step with a liquid containing one or more Group 4 elements and/or Group 5 elements, and then drying and secondarily calcining the resultant. The modified aluminosilicate includes one or more Group 4 elements and/or Group 5 elements, and exhibits an absorbance at 300 nm in an ultraviolet visible spectrum of 1.0 or higher. The method for manufacturing aromatic dihydroxy compounds includes reacting a phenol with hydrogen peroxide in the presence of a specific modified aluminosilicate.

12 Claims, 2 Drawing Sheets

(56) References Cited

OTHER PUBLICATIONS

PCT Written Opinion of the International Searching Authority dated Aug. 20, 2019 filed in PCT/JP2019/019939.

* cited by examiner

[Figure 1]
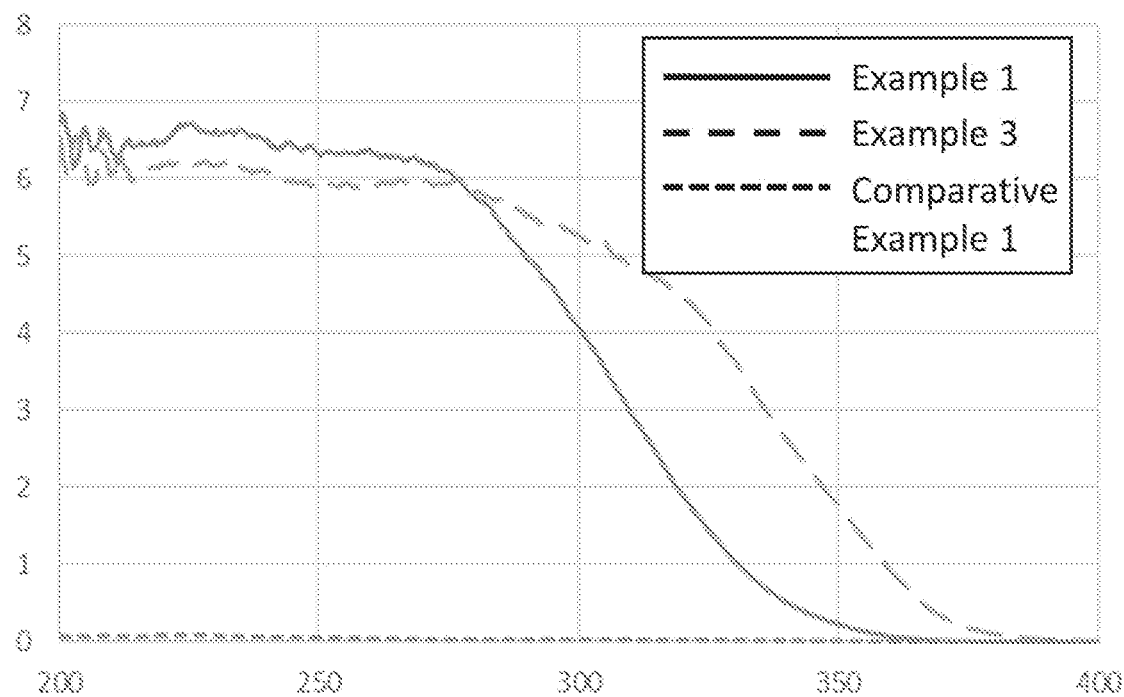

[Figure 2]
X-RAY DIFFRACTION (XRD) MEASUREMENT RESULTS
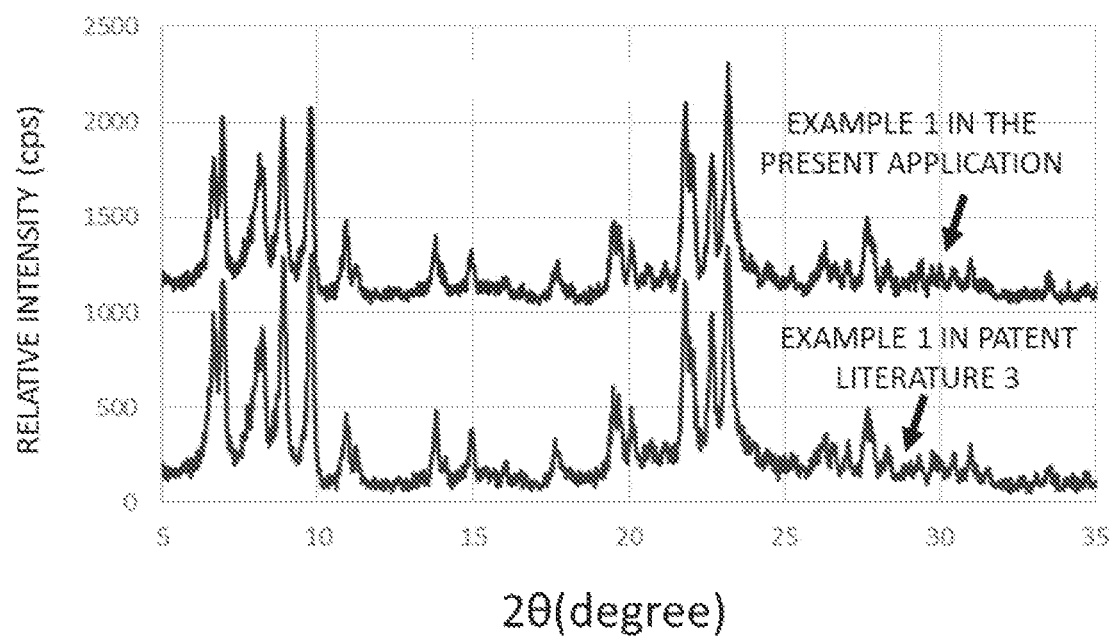

METHOD FOR MANUFACTURING MODIFIED ALUMINOSILICATE, MODIFIED ALUMINOSILICATE, AND METHOD FOR MANUFACTURING AROMATIC DIHYDROXY COMPOUND USING THE SAME

CROSS-REFERENCE TO RELATED APPLICATIONS

This application is a National Phase Application of International Application No. PCT/JP2019/019939, filed May 20, 2019, which claims the priority of Japan Patent Application No. 2018-097032, filed May 21, 2018 and Japan Patent Application No. 2018-097033, filed May 21, 2018. The present application claims priority from both applications and each of these applications is herein incorporated in their entirety by reference.

TECHNICAL FIELD

The present invention relates to a method for manufacturing a modified aluminosilicate, a modified aluminosilicate, and a method for manufacturing an aromatic dihydroxy compound using the same.

BACKGROUND ART

Aromatic dihydroxy compounds are important as intermediates or raw materials for various organic syntheses, and are utilized in the fields of reductants, rubber chemicals, dyes, medicines, agricultural chemicals, polymerization inhibitors, oxidation inhibitors and the like.

The aromatic dihydroxy compounds obtained by reacting a phenol with hydrogen peroxide are, for example, hydroquinone and catechol; the production ratio of hydroquinone and catechol varies depending on manufacturing methods. In recent years, from the demand balance of hydroquinone and catechol, a method for manufacturing particularly hydroquinone highly selectively has earnestly been desired.

In order to manufacture an aromatic dihydroxy compound by reacting a phenol with hydrogen peroxide, there is disclosed a method of using, as a catalyst, a titanosilicate, which is one of crystalline porous silicates (for example, Patent Literature 1 and Patent Literature 2). Further, Patent Literature 3 discloses a titanosilicate obtained by treating an acid-treated aluminosilicate with titanium chloride or titanium alkoxide in a gas phase.

In addition, Patent Literature 4 discloses a method for manufacturing a titanosilicate obtained by mixing a template raw material of aluminosilicate, an aluminum source, a titanium source, a silicon source and an iodide with water to prepare a gel, and heating and crystallizing the gel and then calcining the resultant.

CITATION LIST

Patent Literature

Patent Literature 1: Japanese Patent No. 4254009
Patent Literature 2: International Publication No. WO2015/041137
Patent Literature 3: Japanese Patent Laid-Open No. 2008-050186
Patent Literature 4: Japanese Patent Laid-Open No. 2017-057126

SUMMARY OF INVENTION

Technical Problem

In Patent Literature 3, there is a problem with industrial manufacture since titanium tetrachloride in a gas phase is used and is high in corrosiveness and liable to leak.

For example, although it seems possible to improve the corrosiveness and leakage by devices on the material and the like of the apparatus, there arises the fear of the apparatus becoming costly and the fixed cost rising.

In Patent Literature 4, a titanosilicate is synthesized directly by mixing a template raw material of an aluminosilicate, a titanium source and the like together with water; and a reaction of a phenol with hydrogen peroxide is carried out in the presence of the titanosilicate. In the result of the reaction, it is considered that the yield of hydroquinone is not sufficient from the viewpoint of commercialization.

The present invention has an object to provide a method for manufacturing a modified aluminosilicate by which a hydroquinones can be manufactured highly selectively by a reaction of a phenol with hydrogen peroxide under industrially advantageous conditions. The present invention also has objects to provide a catalyst by which a hydroquinones can be manufactured highly selectively by a reaction of a phenol with hydrogen peroxide, and a method for manufacturing an aromatic dihydroxy compound by using the catalyst under industrially advantageous conditions.

Solution to Problem

As a result of studies to solve the above problems, the present inventors have found that a modified aluminosilicate capable of highly selectively manufacturing hydroquinones can be manufactured by calcining an acid-treated aluminosilicate, preferably an acid-treated crystalline porous aluminosilicate under a specific condition, then contacting the resultant with a liquid containing one or more elements selected from Group 4 elements and Group 5 elements on the periodic table, for example, a titanium source in a liquid phase, and further drying and calcining the resultant; and this finding has led to the completion of a first aspect of the present invention. It has further been found that an aromatic dihydroxy compound (for example, a hydroquinones) can be manufactured highly selectively by reacting a phenol with hydrogen peroxide in the presence of a specific aluminosilicate, preferably a crystalline porous aluminosilicate, having a specific ultraviolet visible spectrum; and this finding has led to the completion of a second aspect of the present invention.

That is, the present invention includes the following items described in [1] to [16].

[1] A method for manufacturing a modified aluminosilicate, comprising a first step of treating an aluminosilicate with an acid, a second step of primarily calcining the treated material obtained in the first step at 550° C. to 850° C., and a third step of contacting the calcined material obtained in the second step with a liquid containing one or more elements selected from the group consisting of Group 4 elements and Group 5 elements on the periodic table, and then drying and secondarily calcining the resultant.

[2] The method for manufacturing a modified aluminosilicate according to [1], wherein the aluminosilicate is a crystalline porous aluminosilicate.

[3] The method for manufacturing a modified aluminosilicate according to [1], wherein the liquid containing the elements is a liquid containing one or more elements selected from the group consisting of Group 4 elements.

[4] The method for manufacturing a modified aluminosilicate according to [1], wherein the liquid containing the elements is a liquid containing titanium.

[5] The method for manufacturing a modified aluminosilicate according to [4], wherein the liquid containing titanium is one or more selected from the group consisting of titanium tetrachloride, a titanium tetrachloride aqueous solution, a titanium trichloride aqueous solution and a titanium sulfate aqueous solution.

[6] The method for manufacturing a modified aluminosilicate according to [2], wherein the crystalline porous aluminosilicate has an MSE framework.

[7] The method for manufacturing a modified aluminosilicate according to [6], wherein the crystalline porous aluminosilicate having an MSE framework is one or more selected from the group consisting of UZM-35, MCM-68 and YNJ-3.

[8] A modified aluminosilicate, comprising one or more elements selected from the group consisting of Group 4 elements and Group 5 elements on the periodic table, and exhibiting an absorbance at 300 nm (A[300]) in an ultraviolet visible spectrum of 1.0 or higher.

[9] The modified aluminosilicate according to [8], wherein the ratio (A[300]/A[210]) of the absorbance at 300 nm (A[300]) in the ultraviolet visible spectrum to an absorbance at 210 nm (A[210]) in the ultraviolet visible spectrum is 0.5 or higher.

[10] The modified aluminosilicate according to [8], wherein the modified aluminosilicate has crystallineness and porousness.

[11] The modified aluminosilicate according to [10], wherein the modified aluminosilicate has an MSE framework.

[12] The modified aluminosilicate according to [8], wherein the element is one or more elements selected from Group 4 elements.

[13] The modified aluminosilicate according to [8], wherein the element is titanium.

[14] The modified aluminosilicate according to [13], wherein the molar ratio ([Si]/[Ti]) of silicon to titanium is in the range of 0.1 to 100.

[15] A catalyst for manufacturing an aromatic dihydroxy compound, comprising a modified aluminosilicate according to [8].

[16] A method for manufacturing an aromatic dihydroxy compound, comprising a step of reacting a phenol with hydrogen peroxide in the presence of a catalyst for manufacturing an aromatic dihydroxy compound according to [15].

Advantageous Effects of Invention

According to the method for manufacturing a modified aluminosilicate according to the first aspect of the present invention, a modified aluminosilicate is enabled to be manufactured by using a liquid having little fear of leakage and containing one or more elements selected from the group consisting of Group 4 elements and Group 5 elements on the periodic table, for example, a titanium source in a liquid phase, and this aspect has an industrially important significance. In addition, by using the modified aluminosilicate manufactured by the above manufacturing method, an aromatic dihydroxy compound, for example, hydroquinone, can be produced highly selectively by a reaction of a phenol with hydrogen peroxide.

According to the aluminosilicate and the method for manufacturing an aromatic dihydroxy compound using the aluminosilicate as a catalyst according to the second aspect of the present invention, an aromatic dihydroxy compound (for example, hydroquinone) can be produced highly selectively by a reaction of a phenol with hydrogen peroxide.

BRIEF DESCRIPTION OF DRAWINGS

FIG. 1 is graphs showing absorbances of crystalline porous aluminotitanosilicates. The abscissa indicates the wavelength (nm), and the ordinate indicates the absorbance.

FIG. 2 is charts showing X-ray diffractometric results of aluminotitanosilicates of Example 1 and Patent Literature 3.

DESCRIPTION OF EMBODIMENTS

Hereinafter, embodiments according to the present invention will be described in detail.

<Method for Manufacturing Modified Aluminosilicate>

First, there will be described a method for manufacturing a modified aluminosilicate, which is the first aspect of the present invention, in which a part of aluminum of an aluminosilicate is considered to be substituted with one or more elements selected from Group 4 elements and Group 5 elements on the periodic table. Here, the aluminosilicate to be used as a raw material preferably contains neither Group 4 elements nor Group 5 elements, or even if containing them, contains them in a degree of not affecting the effects of the present invention. The Group 4 elements include titanium, zirconium and hafnium. The Group 5 elements include vanadium. Among these elements, Group 4 elements are preferable; titanium, zirconium and hafnium are more preferable; and titanium is still more preferable. The above elements can be used singly or may be used concurrently in two or more.

(First Step)

A treatment of the aluminosilicate with an acid is carried out in a first step. The aluminosilicate is preferably crystalline, also preferably porous, and more preferably crystalline and porous. Hereinafter, an aluminosilicate which is crystalline and porous is referred to simply as a crystalline porous aluminosilicate. The crystallineness can be determined from a diffraction pattern by well-known X-ray measurement. The crystalline aluminosilicate preferably has the following structure.

The above aluminosilicate is preferably a porous crystal having parts where an $SiO_4$ tetrahedron having silicon at its center and oxygen arranged at its four vertices and an $AlO_4$ tetrahedron having aluminum arranged in place of the silicon at its center are regularly three-dimensionally connected, in at least a part of the porous crystal. This crystalline porous aluminosilicate more specifically includes zeolite.

The crystalline aluminosilicate to be preferably used in the present invention is not especially limited as long as having the above structure, and is preferably a crystalline porous aluminosilicate having an MSE-type structure (hereinafter, in the present specification, referred to as "MSE framework") in the structural code of The International Zeolite Association, and is especially preferably UZM-35, MCM-68, YNU-3 or the like.

In the method for manufacturing the modified aluminosilicate according to the present invention, since it can be considered that the introduction of a specific element is mainly in the surface of a solid of an aluminosilicate being a raw material, the crystallineness of the aluminosilicate as a raw material can be considered to be mostly maintained even in the modified aluminosilicate as a final product.

The above crystalline porous aluminosilicate having an MSE framework has a three-dimensional pore structure having a ten-membered ring structure composed of 10 units of the above tetrahedron and a twelve-membered ring structure composed of 12 units of the above tetrahedron. It is considered that since the crystalline porous aluminosilicate has pores of the above twelve-membered ring structure, the diffusion inside the pores of the substrate becomes easy and a high catalytic activity is provided. Further, it is considered that since no large cavity is present inside the pores, the para-position selectivity is exhibited in the oxidation reaction of a phenol.

The crystalline porous aluminosilicate having an MSE framework to be used can also be a commercially available product, or can be manufactured by a conventionally well-known method.

For example, UZM-35 can be manufactured by adding dimethyldipropylammonium hydroxide, which is an organic structure-directing agent, an alkali source and a silicon source, then mixing and heating the resultant. UZM-35 can also be manufactured by a method of further adding its seed crystal and an FAU-type zeolite to the raw materials and heating the resultant, or the like.

Use of the seed crystal promotes the crystal growth during the synthesis. The amount of the seed crystal to be added is, in the silicon source fed, preferably 1 to 40% by weight, and preferably 2 to 30% by weight. In addition, the FAU-type zeolite is to be added as a silicon source and an aluminum source, and the amount thereof to be added is preferably 5 to 50% by weight, and more preferably 8 to 40% by weight.

Here, the above seed crystal is not especially limited as long as being a crystalline porous aluminosilicate, and a material having the same crystal structure as that of the modified aluminosilicate as the product can especially suitably be used. Specifically, if a crystalline porous alumino-titanosilicate when the one or more elements selected from Group 4 and Group 5 elements on the periodic table is titanium has an MSE framework, which is a suitable form of the modified aluminosilicate of the present invention, a material having a UZM-35, MCM-68 or YNU-3 structure can suitably be used as the seed crystal.

With regard to the crystallinity of the seed crystal, even one with a low-crystallinity can be used. The crystallinity of the seed crystal is not especially limited, and is preferably 30 to 90%. Here, the crystallinity is determined from the integrated intensity ratio in the X-ray structural diffraction, and is represented as a relative ratio in integrated intensity with the integrated intensity of the crystalline porous aluminosilicate being taken to be 100.

MCM-68 can be manufactured, for example, by a method of adding N,N,N',N'-tetraethylbicyclo[2,2,2]oct-7-ene-2,3:5,6-dipyrrolidinium diiodide, which is an organic structure-directing agent, to a mixed liquid of a silicon source, an aluminum source and an alkali source, and well stirring and heating the resultant.

YNU-3 can be manufactured, for example, by a method of adding an MCM-68 seed crystal to a mixture of N,N,N',N'-tetraethylbicyclo[2,2,2]oct-7-ene-2,3:5,6-dipyrrolidinium diiodide and an alkali source, stirring the resultant, and adding an FAU-type zeolite thereto and heating the resultant.

Examples of the above silicon source include silica, colloidal silica, sodium silicate, wet silica and dry silica. These silicon sources can be used singly or in a combination of two or more.

As the above aluminum source, for example, water-soluble aluminum compounds can be used. Examples of the water-soluble aluminum compounds include aluminum hydroxide, sodium aluminate, aluminum nitrate and aluminum sulfate. These aluminum sources can be used singly or in a combination of two or more.

As the above alkali source, hydroxides containing an alkaline metal can be used. Examples of the hydroxides containing an alkaline metal include sodium hydroxide and potassium hydroxide. These alkali sources can be used singly or in a combination of two or more.

Examples of the acid to be used in the first step include inorganic acids, organic acids and mixtures thereof; and specific examples thereof include nitric acid, hydrochloric acid, sulfuric acid, citric acid, oxalic acid and mixtures thereof. Among these, preferable are acids containing an element selected from Group 15 and Group 16 elements on the periodic table, and especially preferable is nitric acid. The concentration of the acid is not especially limited, and is preferably 5% by weight to 80% by weight, and more preferably 40% by weight to 80% by weight. In the case of using the acid as an aqueous solution, the amount thereof to be used is, per part by mass of the crystalline porous aluminosilicate, preferably 10 to 100 parts by mass, and more preferably 20 to 100 parts by mass.

The temperature condition of treatment with the above acid is preferably 50° C. to 170° C., and more preferably 130° C. to 170° C. The time of the treatment of the acid is preferably 5 hours to 48 hours, and more preferably 12 hours to 36 hours. The still more preferable lower limit of the time is 18 hours. By the treatment with an acid, a part of aluminum is removed from the aluminosilicate. It is presumed that mainly aluminum of the surface of the aluminosilicate is removed. It is presumed that by the treatment under the conditions of the relatively high temperature and long time as described above, in a step of calcination in a second step described later, it becomes easy for a structure advantageous for incorporation of the above Group 4 elements and Group 5 elements to be formed.

(Second Step)

In the second step, the acid-treated material obtained in the above first step is subjected to primary calcination. A method of calcination is not especially limited, and examples thereof include methods of calcination using an electric furnace, a gas furnace, or the like. The conditions of calcination preferably involve heating in the air atmosphere for 0.1 hours to 20 hours. The temperature of calcination is 550° C. to 850° C., and more preferably 600° C. to 800° C. It is presumed that by the primary calcination in this relatively high-temperature environment, an environment is provided which is advantageous for forming the modified aluminosilicate containing a Group 4 element, in which titanium is a typical species, or a Group 5 element, in a high-activity state.

Before the calcination of the above acid-treated material, the treated material is preferably filtered by using a Nutche filter or the like to separate the acid (aqueous solution) used and the like; and then the residue is washed with water and dried. The cleaning step is preferably carried out without being dried and with a wet state being held. A method of drying is not especially limited, and homogeneous and quick drying is preferable, and, for example, an external heating system such as hot-air drying or superheated steam drying, or an electromagnetic heating system such as microwave heat drying or high-frequency dielectric heat drying can be used.

(Third Step)

In a third step, the primarily calcined material obtained in the second step described above is contacted with a liquid containing one or more elements selected from Group 4 elements and Group 5 elements on the periodic table as element sources in a liquid phase state, and dried and subjected to secondary calcination. Hereinafter, a form using a liquid containing titanium (titanium source in a liquid phase), which is the most preferable form, will be interpreted as a representative example.

The titanium source in a liquid phase is a liquid containing titanium. Examples of the liquid containing titanium include titanium compounds themselves in liquid form and aqueous solutions of titanium compounds. Among these, titanium compounds exhibiting substantially acidity in the liquid state are a preferable form.

Examples of the titanium compound in liquid form include titanium tetrachloride ($TiCl_4$) and tetrabutoxytitanium; among these, titanium tetrachloride is preferable. Examples of the solutions of titanium compounds include a titanium tetrachloride aqueous solution, a titanium trichloride ($TiCl_3$) aqueous solution, a titanium sulfate ($Ti(SO_4)_2$) aqueous solution and a potassium hexafluorotitanate aqueous solution. Among these, preferable are a titanium tetrachloride aqueous solution, a titanium trichloride aqueous solution and a titanium sulfate aqueous solution. In the present invention, also in the case of using a titanium source having low reactivity such as titanium trichloride or titanium sulfate other than titanium tetrachloride, the catalytic activity described later can be developed. These liquids containing titanium can be used singly or in a combination of two or more. As the above liquid containing titanium, commercially available ones can also be used and ones suitably prepared by diluting a solid titanium compound with water to a desired concentration can also be used. Since a titanium source in a liquid phase (liquid containing titanium) more hardly leaks than a titanium source in a gas phase, and is improved in the problem with corrosion of manufacturing machines, analytical devices and the like, it becomes easy for the industrial manufacture to be carried out.

The condition of adding the titanium source to the above primarily calcined material is not especially limited, and such a condition is preferable that titanium is carried on the crystalline porous aluminosilicate, for example, a part of aluminum can be substituted with titanium. For example, in the case of using a titanium compound itself in liquid form, the titanium compound in liquid form is added, per g of the primarily calcined material, preferably in 5 to 300 parts by weight, and more preferably in 20 to 250 parts by weight. In the case of using an aqueous solution of a titanium compound, the aqueous solution of a titanium compound is added, per part by weight of the primarily calcined material, preferably in 1 to 10 parts by weight, and more preferably in 1 to 7 parts by weight. The concentration of the above aqueous solution is, depending on a compound to be used, for example, 10 to 70% by weight, and preferably 15 to 60% by weight.

With regard to the amount of the titanium compound in the above aqueous solution, the lower limit value per 1 g of the primarily calcined material is preferably 0.1 g, more preferably 0.2 g, still more preferably 0.3 g, and especially preferably 0.5 g. On the other hand, the upper limit value is preferably 10 g, more preferably 5 g, and still more preferably 3 g.

In the case of adding the above titanium source, as long as the total amount to be added is in the range of the above amount to be added, the addition may be carried out in one time, or may be carried out in a plurality of times by repeating the third step. For example, the titanium source is added to the primarily calcined material, and the titanium source may be added again to a calcined material obtained by carrying out drying and secondary calcination described later, and subjected to drying and secondary calcination. When the above titanium source is added, since hydrochloric acid is generated by a reaction of moisture in the air with the titanium compound, the addition is preferably carried out in a nitrogen atmosphere.

After sufficiently mixing the primarily calcined material and the titanium source added followed by drying the resulting mixture fully by being subjected to heating treatment or by a method similar to the drying method in the second step, the resultant is subjected to secondary calcination. The temperature in the heating treatment or the drying step described above is not especially limited, and is, for example, in order to effectively incorporate titanium in the aluminosilicate, preferably in the range of 20 to 150° C. The lower limit value thereof is more preferably 30° C., still more preferably 40° C., and especially preferably 50° C. On the other hand, the upper limit value thereof is more preferably 140° C., still more preferably 120° C., and especially preferably 100° C. The time necessary for the above step is also not especially limited, and is preferably 0.1 to 24 hours. The lower limit value thereof is more preferably 0.3 hours, still more preferably 0.4 hours, and especially preferably 0.5 hours. On the other hand, the upper limit value thereof is more preferably 12 hours, and still more preferably 6 hours. A method of carrying out the secondary calcination is not especially limited, and the calcination can be carried out, for example, by using an electric furnace, or a gas furnace. The conditions of calcination are: in the air atmosphere; at 400° C. or higher and 800° C. or lower; and for 0.1 to 20 hours. By this step, a crystalline porous aluminotitanosilicate in which a part of aluminum in the crystalline porous aluminosilicate which seems to be substituted with titanium can be obtained.

The secondary calcination may be carried out after: the mixture of the titanium source and the primarily calcined material is heated to preliminarily remove moisture before the above drying step; then, the mixture is filtered to remove foreign substances; cleaning operation using an organic solvent is carried out; and otherwise.

The above manufacturing conditions can apply to the cases of using elements other than titanium.

As examples of compounds containing a Group 4 element on the periodic table usable in place of the above titanium source, zirconium tetrachloride, tetraalkoxyzirconiums, hafnium tetrachloride, tetraalkoxyhafniums, and zirconium sulfate can be used, as required, by being made into a liquid state by concurrently using water, an alcohol, an ether or the like. Examples thereof include aqueous solutions, alcohol solutions and ether solutions of these compounds. As examples of compounds containing a Group 5 element on the periodic table usable in place of the above titanium source, vanadium pentachloride, vanadium sulfate, vanadyl trichloride, and alkoxy-substituted compounds thereof can be used, as required, by being made into a liquid state by concurrently using water, an alcohol, an ether or the like. Examples thereof include aqueous solutions, alcohol solutions and ether solutions of these compounds.

The modified aluminosilicate according to the present invention preferably has crystallineness similarly to the aluminosilicate being a raw material; and being porous is also preferable. The crystallineness may be quite all right to be considered to be the same state as in the interpretation of the aluminosilicate being a raw material.

It is well known that porous compounds have a large specific surface area. The specific surface area of the modified aluminosilicate of the present invention is preferably 50 to 1000 $m^2/g$. The lower limit value of the specific surface area is more preferably 100 $m^2/g$, and still more preferably 150 $m^2/g$. On the other hand, the upper limit value of the specific surface area is more preferably 800 $m^2/g$, and still more preferably 600 $m^2/g$.

The value of the specific surface area described above can be determined by fabricating a BET plot from a measurement result using the well-known nitrogen adsorption/desorption measuring method (using, for example, BELSORP-max, manufactured by MicrotrackBell Corp.) and by the well-known calculation process based on the BET theory.

The range of the pore volume of the modified aluminosilicate of the present invention is preferably 0.1 to 0.5 $cm^3/g$, and still more preferably 0.2 to 0.4 $cm^3/g$.

<Modified Aluminosilicate>

Then, there will be described a modified aluminosilicate, which is the second aspect of the present invention, having a characteristic in absorption in a specific wavelength region in ultraviolet visible absorption spectrometry.

The modified aluminosilicate in the present invention comprises elements selected from the group consisting of Group 4 elements and Group 5 elements on the periodic table, and exhibits an absorbance at 300 nm (A[300]) in an ultraviolet visible spectrum of 1.0 or higher. Specific examples, suitable examples and the like of the elements selected from Group 4 and Group 5 elements contained in the modified aluminosilicate of the present invention are the same as in the above description of the method for manufacturing a modified aluminosilicate according to the first aspect of the present invention.

The modified aluminosilicate of the present invention preferably has crystallineness and porousness. The modified aluminosilicate having the crystallineness and porousness preferably has an MSE framework. The crystallineness and the porousness are the same as in the above interpretations of the first aspect of the present invention.

The modified aluminosilicate of the present invention is preferably a crystalline porous aluminotitanosilicate obtained by such a method that a part of aluminum contained in the crystalline porous aluminosilicate having the crystallineness and the porousness is substituted with titanium.

The above crystalline porous aluminosilicate is a porous crystal having parts where an $SiO_4$ tetrahedron having silicon at its center and oxygen arranged at its four vertices and an $AlO_4$ tetrahedron having aluminum arranged in place of the silicon at its center are regularly three-dimensionally connected, in at least a part of the porous crystal and is typically one of zeolites containing aluminosilicate. The modified aluminosilicate having crystallineness and porousness comprises aluminum and one or more elements selected from the group consisting of Group 4 elements and Group 5 elements on the periodic table in the above crystalline porous aluminosilicate framework, and is preferably obtained by such a method that a part of aluminum in the crystalline porous aluminosilicate framework is substituted with one or more elements selected from the group consisting of Group 4 elements and Group 5 elements on the periodic table. For example, when the one or more elements selected from the group consisting of Group 4 elements and Group 5 elements on the periodic table is titanium, the crystalline porous modified aluminosilicate becomes the crystalline porous aluminotitanosilicate, which comprises aluminum and titanium in its aluminosilicate framework, and is preferably obtained by such a method that a part of aluminum in its framework is substituted with titanium.

The content of the Group 4 elements and Group 5 elements contained in the modified aluminosilicate of the present invention is not especially limited. For example, when titanium is contained as the one or more elements selected from the group consisting of the Group 4 elements and Group 5 elements contained in the above modified aluminosilicate, the molar ratio ([Si]/[Ti]) of silicon to titanium is preferably in the range of 0.1 to 100, more preferably in the range of 0.5 to 50, still more preferably in the range of 1 to 30, and most preferably in the range of 2 to 30.

In the case of using a compound easily crystallizable by itself like $TiCl_3$, there is such a possibility that the element is incorporated in cluster form or crystal form in the surface of aluminosilicate. In this case, since the apparent content of the element increases in some cases, the [Si]/[Ti] ratio is likely to become a low value. The range of the [Si]/[Ti] ratio in such a case is preferably 0.5 to 30. The lower limit value thereof is more preferably 1, and still more preferably 1.2. On the other hand, the upper limit value thereof is more preferably 20, and still more preferably 15.

The content of aluminum in the modified aluminosilicate of the present invention is not especially limited, and is, in terms of molar ratio ([Si]/[Al]) of silicon to aluminum, preferably in the range of 5 to 100000, more preferably in the range of 10 to 10000, and most preferably in the range of 100 to 1000.

When the A[300] is lower than 1.0, when an aromatic dihydroxy compound is manufactured by a reaction of a phenol with hydrogen peroxide, the selectivity of the aromatic dihydroxy compound is likely to be relatively low. Here, the measuring method of the absorbance is not especially limited, and the absorbance may be a result measured by either of a transmission method and a reflection method. In the case of measuring by the reflection method, although there are cases where reflected light contains diffused reflected light and the like other than regular reflected light, the absorbance is calculated, for convenience, by assuming all the light to be regular reflected light.

Although the detailed mechanism is unclear, the present inventors presume as follows (hereinafter, there will be interpreted as an example, the crystalline porous aluminotitanosilicate in which an element selected from the Group 4 and Group 5 elements is titanium).

It is presumed that aluminum and titanium are present in the framework surface part of the crystalline porous aluminotitanosilicate. In addition, it can be considered that these are present preferably dominantly in the inside of recesses of pores and the like of the crystalline porous aluminotitanosilicate. Here, for example, in the case of such a mode that an aluminotitanosilicate is manufactured by a method using high-temperature titanium tetrachloride in a gas state as described in Patent Literature 3, and seems to contain only titanium completely incorporated without defects as the framework of the crystal structure, it is presumed that it is difficult for the absorbance nearly at 300 nm in the ultraviolet visible spectrum to become 1.0 or higher. In other words, it is presumed that in such a crystalline porous aluminotitanosilicate as satisfying the requirements of the present invention, much of titanium is present which is incorporated incompletely in its basic framework structure and assumes an unstable structure. It is presumed that such a titanium species contributes largely to a reaction of forming aromatic dihydroxy compounds, and when the oxidation reaction of a phenol with hydrogen peroxide progresses, due to its instability, there are suppressed the production of 1,2-hydroxy compounds (for example, catechol), which are considered to be conformationally disadvantageous, and the production of benzoquinone, which is a form more progressed in the reaction, while 1,4-type aromatic dihydroxy compounds can be manufactured highly selectively.

From the viewpoint of more enhancing the selectivity of the aromatic dihydroxy compound, the lower limit value of A[300] of the modified aluminosilicate is preferably 1.5, and more preferably 1.8. On the other hand, the upper limit value of A[300], though the setting thereof has no essential significance, is preferably 15, and more preferably 10. In addition, the A[300] is 0.2 or lower for usual crystalline porous aluminotitanosilicates.

In addition, the ratio (A[300]/A[210]) of the A[300] to an absorbance at 210 nm (A[210]) in the ultraviolet visible spectrum is preferably 0.5 or higher, more preferably 0.6 or higher, and most preferably 0.8 or higher. For example, in the case of containing titanium incorporated without defects in the framework of the crystal structure, since the A[210] becomes relatively higher than the A[300], the A[300]/A[210] usually becomes 0.1 or lower for usual crystalline porous aluminotitanosilicates. The upper limit value of the above A[300]/A[210] is, though having no special significance, preferably 1.5, and more preferably 1.0.

The modified aluminosilicate according to the present invention is not especially limited as long as having the above structure and further having the above-mentioned ultraviolet visible spectrum characteristic, and is preferably a crystalline porous aluminosilicate having an MSE-type structure (hereinafter, in the present specification, referred to as "MSE framework") in the structural code of The International Zeolite Association, and more preferably a crystalline porous aluminosilicate having a UZM-35, an MCM-68 or a YNU-3 structure.

The above crystalline porous aluminosilicate having an MSE framework has a three-dimensional pore structure having a ten-membered ring structure composed of 10 units of the above tetrahedron and a twelve-membered ring structure composed of 12 units of the above tetrahedron. It is considered that since the crystalline porous aluminosilicate has pores of the above twelve-membered ring structure, the diffusion inside the pores of the substrate becomes easy and a high catalytic activity is provided. Further, it is considered that since no large cavity is present inside the pores, the para-position selectivity is exhibited in the oxidation reaction of a phenol.

The crystalline porous aluminosilicate having an MSE framework can be preferably obtained by such a method that aluminum of a crystalline porous aluminosilicate having an MSE framework is substituted with an element selected from Group 4 and Group 5 elements on the periodic table. The above element is preferably a Group 4 element, and especially preferably titanium. The crystalline porous aluminosilicate having an MSE framework is the similar one as in the first aspect of the present invention.

Examples of a method of obtaining the modified aluminosilicate of the present invention include the method for manufacturing a modified aluminosilicate according to the first aspect of the present invention.

(Method for Manufacturing Aromatic Dihydroxy Compound)

There will be described a method for manufacturing an aromatic dihydroxy compound by reacting a phenol with hydrogen peroxide in the presence of the modified aluminosilicate obtained by the above manufacturing method according to the first aspect of the present invention or the modified aluminosilicate according to the second aspect of the present invention. The modified aluminosilicate according to the second aspect of the present invention can be used without any especial limitations as long as the modified aluminosilicate is one exhibiting an absorbance at 300 nm (A[300]) of its ultraviolet visible spectrum of 1.0 or higher, and is preferably a crystalline porous aluminosilicate obtained by such a method that a part of aluminum contained in a crystalline porous aluminosilicate is substituted with an element selected from Group 4 and Group 5 elements on the periodic table. The above element is preferably a Group 4 element, and especially preferably titanium.

The phenols to be used in the present invention mean a non-substituted phenol and substituted phenols. Here, examples of the substituted phenols include alkylphenols substituted with a straight-chain or branched alkyl group(s) having 1 to 6 carbon atoms, such as a methyl group, an ethyl group, an isopropyl group, a butyl group or a hexyl group, or a cycloalkyl group(s).

Examples of the phenols include phenol, 2-methylphenol, 3-methylphenol, 2,6-dimethylphenol, 2,3,5-trimethylphenol, 2-ethylphenol, 3-isopropylphenol, 2-butylphenol and 2-cyclohexylphenol; among these, phenol is preferable. When phenols have substituents on both of the 2-position and the 6-position thereof, products are hydroquinone derivatives only.

Examples of the aromatic dihydroxy compounds being reaction products include hydroquinones (substituted or non-substituted hydroquinones) and catechols (substituted or non-substituted catechols); specific examples thereof include hydroquinone, catechol, 2-methylhydroquinone, 3-methylcatechol, 4-methylcatechol, 3-methylhydroquinone, 1,4-dimethylhydroquinone, 1,4-dimethylcatechol, 3,5-dimethylcatechol, 2,3-dimethylhydroquinone and 2,3-dimethylcatechol.

The modified aluminosilicate obtained in the present invention is used as a catalyst when the aromatic dihydroxy compound is manufactured. As packing systems of the catalyst, there are adopted various types of systems, such as a fixed bed, a fluidized bed, a suspension bed and a tray fixed bed, and any one thereof may be adopted with no problem. The above catalyst may be used as it is, and may also be used by being molded so as to be adapted to the packing system of the catalyst. As molding methods of the catalyst, usual are extrusion molding, tableting molding, tumbling granulation, spray granulation and the like. In the case of using the catalyst in a fixed bed system, extrusion molding and tableting molding are preferable. In the case of a suspension bed system, spray granulation is preferable. After the spray granulation, drying and calcination may be carried out. The average particle diameter of a spray granulated catalyst is preferably in the range of 0.1 μm to 1000 μm, and more preferably in the range of 5 μm to 100 μm. When the average particle diameter is 0.1 μm or larger, the case is preferable because filtration and the like of the catalyst are easy in handling; and when being 1000 μm or smaller, the case is preferable because the catalyst is good in performance and high in strength.

The amount of the above catalyst to be used is, based on the total mass of a reaction liquid (total mass of liquid components in a reaction system, not containing masses of fixed components), in outer ratio, preferably in the range of 0.1 to 30% by mass, and more preferably in the range of 0.4 to 20% by mass. When the amount is 0.1% by mass or larger, the case is preferable because the reaction is completed in a short time and the productivity is improved. When being 30% by mass or smaller, the case is preferable in that the amount of the catalyst to be separated and recovered is small.

In the case of using, as the catalyst for a method for manufacturing an aromatic dihydroxy compound, the modified aluminosilicate obtained by the manufacturing method according to the first aspect of the present invention or the modified aluminosilicate according to the second aspect of the present invention, the modified aluminosilicate can be combined with other components. Examples of the other components include a siloxane compound described in Patent Literature 1 and a specific alcohol compound described in Patent Literature 2. Such a component is preferably used in such a proportion as becoming 5 to 90% by mass of the above reaction liquid. More preferable is 8 to 90% by mass.

Then, hydrogen peroxide is made to be, with respect to phenols, in molar ratio, preferably 0.01 or higher and 1 or lower. The concentration of the hydrogen peroxide to be used is not especially limited, and a usual 30%-concentration aqueous solution thereof may be used; a higher-concentration hydrogen peroxide aqueous solution may be used as it is or may be diluted with an inactive solvent and used in the reaction system. The solvent to be used for the dilution includes alcohols and water. The hydrogen peroxide may be added at once, or may be added gradually over some time.

The reaction temperature is preferably in the range of 30° C. to 130° C., and more preferably in the range of 40° C. to 100° C. Although the reaction progresses also at a temperature out of this temperature range, from the viewpoint of improving the productivity, the above range is preferable. The reaction pressure is not especially limited.

A system for the above reaction is not especially limited, and any of a batch system, a semi-batch system and a continuous system may be used for carrying out the reaction. In the case of using the continuous system, the reaction may be carried out in a suspension bed type-homogeneous mixing tank, in a fixed-bed flow type plug flow system, or in a plurality of reactors connected in series and/or in parallel. From the viewpoint of apparatus costs, the number of reactors is preferably made to be one to four. In the case of using a plurality of reactors, the hydrogen peroxide may be added dividedly thereto.

In order to obtain the aromatic dihydroxy compound from the reaction liquid, a refining treatment such as removal of unreacted components and by-products may be carried out on the reaction liquid or a separated liquid containing the dihydroxy compound after the above catalyst is separated. It is suitable that the refining treatment is carried out on the separated liquid containing the aromatic dihydroxy compound after the catalyst is separated.

A method of the refining treatment is not especially limited, and specifically includes oil water separation, extraction, distillation, crystallization, and combinations thereof. A method, procedure and the like of the refining treatment are not especially limited, and for example, by the following method, the reaction liquid and the separated liquid containing the aromatic dihydroxy compound after the above catalyst is separated can be refined.

When the reaction liquid separates into an oil phase and a water phase, the oil water separation is possible. By the oil water separation, the water phase having a low content of the dihydroxy compound is removed and the oil phase is recovered. In this case, the aromatic dihydroxy compound may be recovered from the separated water phase by extraction or distillation, or a part or the whole of the separated water phase may be again used for the reaction. Further, the catalyst separated in the above catalyst separation step or the catalyst having been subjected to drying treatment is dispersed in the separated water phase and can also be supplied to the reactor. On the other hand, it is desirable that the oil phase is further subjected to a refining treatment by extraction, distillation, crystallization or the like.

A solvent, for example, 1-butanol, toluene, isopropyl ether or methyl isobutyl ketone is used for the extraction. By combining the extraction with the oil water separation, the above oil water separation can efficiently be carried out. The extracting solvent is preferably separated and recovered by a distillation column, and recycled and used.

The distillation may be carried out on the reaction liquid right after the separation of the catalyst, or may be carried out on the oil phase and the water phase after the above oil water separation. An extract liquid may be further distilled.

In the case of distilling the reaction liquid right after the separation of the catalyst, lower boiling components such as water and alcohols are preferably separated first. The water and alcohols may be separated by separate distillation columns, or may be separated by one distillation column.

After water and alcohols are separated by the above-mentioned oil water separation, extraction, distillation operation or the like, phenols may be recovered by a next distillation operation and again used for the reaction. When recovered phenols contain water which cannot completely be separated, the water can be removed by azeotropic distillation with isopropyl ether or toluene added to the recovered phenols.

The azeotropic distillation can also be carried out on water before the recovery of a phenol or a liquid after the separation of alcohols. The separated water may be again used for the reaction, or may also be made wastewater. When the recovered phenols contain impurities such as reaction by-products other than water, the impurities can also be separated further by distillation operation. When the impurities are benzoquinones as reaction by-products, the benzoquinones can be again supplied to the reactor together with the phenols.

After the separation of the phenols, higher boiling components than the aromatic dihydroxy compound are removed by distillation and hydroquinones and catechols can be separated by a next distillation operation. With regard to separation of the higher boiling components and hydroquinones and catechols, the hydroquinones can also be separated by one distillation operation by being extracted from a middle stage of a distillation column.

The purity of the obtained hydroquinones and catechols can be raised by removing impurities, as required, by distillation or crystallization.

When for example, phenol and hydrogen peroxide are reacted in the presence of the modified aluminosilicate according to the present invention, hydroquinone is likely to be produced in a high yield. Further, hydroquinone is likely to be produced in a higher selectivity than catechol and benzoquinone. Hence, it can be said that the modified aluminosilicate according to the present invention is high in the industrial value.

EXAMPLES

Hereinafter, the present invention will be described in more detail by way of Examples, but the present invention is not limited to these Examples at all.

(Preparation of UZM-35)

A UZM-35 having an MSE framework was prepared by the following method.

First, 15.8 g of a 4.8-mmol/g NaOH aqueous solution, 15.9 g of a 4.7-mmol/g KOH aqueous solution, 31.5 g of a 40 wt % dimethyldipropylammonium hydroxide aqueous solution and 55 g of a colloidal silica (product name: LUDOX(R) AS-40, manufactured by Sigma-Aldrich Corp.) were placed in a vessel, and stirred at 60° C. to thereby obtain a gelatinous substance.

Then, 1.49 g of a UZM-35 seed crystal and 10.2 g of an FAU-type zeolite (product name: HSZ-HUA350, manufactured by Tosoh Corp.) were added to the obtained gelatinous substance, and mixed, and then, the mixture was put in an autoclave and heated at 160° C. for 68 hours. A cooled mixture was filtered and washed with water and air-dried for one day, and then calcined at 500° C. for 10 hours to thereby obtain a UZM-35.

Titanium tetrachloride, a titanium tetrachloride aqueous solution, a titanium trichloride aqueous solution and a titanium sulfate aqueous solution used were commercially available reagents of the following manufacturers.

Titanium tetrachloride: manufactured by Kishida Chemical Co., Ltd.

Titanium tetrachloride aqueous solution: manufactured by FUJIFILM Wako Pure Chemical Corp.

Titanium trichloride aqueous solution: manufactured by Kanto Chemical Co., Inc.

Titanium sulfate aqueous solution: manufactured by Kanto Chemical Co., Inc.

Example 1

(Dealuminating Treatment of the UZM-35)

3 g of the UZM-35 prepared in the above and 120 g of a 60% nitric acid were placed in a vessel and mixed, and then, the mixture was put in an autoclave and heated at 148° C. for 24 hours. A cooled mixture was filtered and washed with water and air-dried for one day, and then subjected to primary calcination at 600° C. for 2 hours to thereby obtain a UZM-35 (hereinafter, referred to as "dealuminated UZM-35") in which a part of aluminum in the UZM-35 had been eliminated.

(Preparation of Ti-UZM-35 Catalyst)

In a nitrogen atmosphere, 2 g of the dealuminated UZM-35 obtained in the above was put in a glass vessel; 173 g (100 ml) of titanium tetrachloride was added thereto and mixed and subjected to a heat treatment at 120° C. for 1 hour. A cooled mixture was filtered and washed with toluene and hexane, and then deaerated and dried. The resultant was then subjected to secondary calcination at 600° C. for 2 hours to thereby obtain a crystalline porous aluminotitanosilicate (hereinafter, referred to as "Ti-UZM-35 catalyst") in which a part of aluminum of the dealuminated UZM-35 may have been substituted with titanium. As a result of measurement by a nitrogen adsorption/desorption method described later, the specific surface area was 260 m$^2$/g.

Example 2

1 g of the dealuminated UZM-35 prepared in the above was put in a vessel, and vacuum deaerated by using an evaporator at 60° C. for 1 hour. 5 g of a 50% titanium tetrachloride aqueous solution was added thereto, and deaerated and dried at 70° C. for 1 hour. The dried material was subjected to secondary calcination at 600° C. for 2 hours to thereby obtain a Ti-UZM-35 catalyst of Example 2.

Example 3

A Ti-UZM-35 catalyst of Example 3 was obtained by preparation under the same conditions as in Example 2, except for altering the 50% titanium tetrachloride aqueous solution to a 20% titanium trichloride aqueous solution.

Example 4

A Ti-UZM-35 catalyst of Example 4 was obtained by preparation under the same conditions as in Example 2, except for altering the 50% titanium tetrachloride aqueous solution to a 30% titanium sulfate aqueous solution.

Example 5

A Ti-UZM-35 catalyst of Example 5 was obtained by preparation under the same conditions as in Example 3, except for altering the primary calcination temperature in preparation of a dealuminated UZM-35 to 700° C.

Example 6

A Ti-UZM-35 catalyst of Example 6 was obtained by preparation under the same conditions as in Example 3, except for altering the primary calcination temperature in preparation of a dealuminated UZM-35 to 800° C.

Example 7

A Ti-UZM-35 catalyst of Example 7 was obtained by preparation under the same conditions as in Example 3, except for altering the amount of the 20% titanium trichloride aqueous solution used to 3 g. As a result of measurement by the nitrogen adsorption/desorption method, the specific surface area was 240 m$^2$/g.

Example 8

A Ti-UZM-35 catalyst of Example 8 was obtained by preparation under the same conditions as in Example 3, except for altering the amount of the 20% titanium trichloride aqueous solution used to 7 g.

Example 9

1 g of the Ti-UZM-35 catalyst obtained in Example 3 was put in a vessel, and vacuum deaerated by using an evaporator at 60° C. for 1 hour. 5 g of the 20% titanium trichloride aqueous solution was added thereto and deaerated and dried at 70° C. for 1 hour. The dried material was subjected to secondary calcination at 600° C. for 2 hours to thereby obtain a Ti-UZM-35 catalyst of Example 9.

Example 10

A Ti-UZM-35 catalyst of Example 10 was obtained by preparation under the same conditions as in Example 3, except for altering the amount of the 20% titanium trichloride aqueous solution used to 1 g.

Comparative Example 1

A catalyst of Comparative Example 1 was obtained by preparation under the same conditions as in Example 1, except for altering the primary calcination temperature to 120° C.

Comparative Example 2

A Ti-UZM-35 catalyst of Comparative Example 2 was obtained by preparation under the same conditions as in Example 3, except for carrying out no primary calcination (carrying out natural drying (air-drying) at 20° C.).

Comparative Example 3

A Ti-UZM-35 catalyst of Comparative Example 3 was obtained by preparation under the same conditions as in Example 3, except for altering the primary calcination temperature to 400° C.

Comparative Example 4

A Ti-UZM-35 catalyst of Comparative Example 4 was obtained by preparation under the same conditions as in Example 3, except for altering the primary calcination temperature to 500° C.

Comparative Example 5

The preparation was carried out under the same conditions as in Example 3, except for altering the primary calcination temperature in preparation of a dealuminated UZM-35 to 900° C. As a result of an XRD measurement, however, since the crystal structure of UZM-35 collapsed, a target Ti-UZM-35 catalyst could not be obtained.

Comparative Example 6

A catalyst was prepared by the same method as in Example 1 described in Patent Literature 3.

Comparative Example 7

A catalyst was prepared by the same method as in Example 1 described in Patent Literature 4.

Reference Example 1 g of the dealuminated UZM-35 prepared in Example 1 was put in a vessel, and vacuum deaerated at 60° C. for 1 hour by using an evaporator. 1 g of the 20% titanium trichloride aqueous solution was added thereto, and subjected to heat treatment at 160° C. for 4 hours. The heat treated material was cooled and filtered, and then subjected to secondary calcination at 600° C. for 2 hours to thereby obtain a Ti-UZM-35 catalyst of Reference Example.

(Performance Evaluations of Each Catalyst)

Hydroquinone (HQ), catechol (CA) and benzoquinone (BQ) produced by reacting a phenol with hydrogen peroxide in the presence of each catalyst obtained in the above Examples 1 to 10, Comparative Examples 1 to 4 and Reference Example 1 were measured by a measuring method described later. From obtained results, the hydroquinone yield (HQ yield) (%), the hydroquinone/catechol ratio (HQ/CA ratio), the benzoquinone yield (BQ yield) (1) and the hydroquinone/benzoquinone ratio (HQ/BQ ratio) were calculated by the following expressions. Results are shown in Table 1.

Hydroquinone yield(%)=(number of moles of produced hydroquinone)/(number of moles of hydrogen peroxide)×100

Since hydrogen peroxide is partially decomposed into water and oxygen in the course of the reaction, the hydrogen peroxide utilization efficiency is defined as follows.

Hydrogen peroxide utilization efficiency=[(number of moles of produced hydroquinone)+(number of moles of produced catechol)+(number of moles of produced benzoquinone)]/number of moles of hydrogen peroxide By using the above expression, the hydroquinone yield could also be represented by the following expression.

Hydroquinone yield(%)=(hydrogen peroxide utilization efficiency)×(number of moles of produced hydroquinone)/[(number of moles of produced hydroquinone)+(number of moles of produced catechol)+(number of moles of produced benzoquinone)]×100

Hydroquinone/catechol ratio=(number of moles of produced hydroquinone)/(number of moles of produced catechol)Hydroquinone/benzoquinone ratio=(number of moles of produced hydroquinone)/(number of moles of produced benzoquinone)

Benzoquinone yield(%)=(number of moles of produced benzoquinone)/(number of moles of hydrogen peroxide)×100

By using the above-mentioned "hydrogen peroxide utilization efficiency", the benzoquinone yield could also be defined as follows.

Benzoquinone yield(%)=(hydrogen peroxide utilization efficiency)×(number of moles of produced benzoquinone)/[(number of moles of produced hydroquinone)+(number of moles of produced catechol)+(number of moles of produced benzoquinone)]×100

TABLE 1

| | Primary Calcination Temperature (° C.) | Titanium Source | Amount of Titanium Source Added * | Crystal-lineness | Absorb-ance [300 nm] | Absorb-ance Ratio A[300]/A[210] | Si/Ti Ratio (m.r.) | HQ Yield (wt %) | HQ/CA Ratio | BQ Yield (wt %) | HQ/BQ Ratio | Specific Surface Area (m$^2$/g) |
|---|---|---|---|---|---|---|---|---|---|---|---|---|
| Example 1 | 600 | TiCl$_4$ | 50 ml | AA | 5.260 | 0.639 | 17.0 | 47.70 | 10.90 | 0.29 | 164.20 | 260 |
| Example 2 | 600 | TiCl$_4$ aqueous solution | 5 g | AA | 3.368 | 0.614 | 14.0 | 52.10 | 4.29 | 5.52 | 9.44 | — |
| Example 3 | 600 | TiCl$_3$ aqueous solution | 5 g | AA | 4.060 | 0.864 | 2.4 | 49.90 | 4.74 | 4.58 | 10.90 | — |
| Example 4 | 600 | Ti(SO$_4$)$_2$ aqueous solution | 5 g | AA | 3.713 | 0.597 | 11.0 | 53.20 | 5.26 | 4.61 | 11.54 | — |
| Example 5 | 700 | TiCl$_3$ aqueous solution | 5 g | AA | — | — | — | 50.10 | 7.30 | 3.52 | 14.23 | — |

TABLE 1-continued

| | Primary Calcination Temperature (° C.) | Titanium Source | Amount of Titanium Source Added * | Crystallineness | Absorbance [300 nm] | Absorbance Ratio A[300]/A[210] | Si/Ti Ratio (m.r.) | HQ Yield (wt %) | HQ/CA Ratio | BQ Yield (wt %) | HQ/BQ Ratio | Specific Surface Area (m²/g) |
|---|---|---|---|---|---|---|---|---|---|---|---|---|
| Example 6 | 800 | TiCl₃ aqueous solution | 5 g | AA | — | — | — | 31.90 | 5.00 | 9.24 | 3.45 | — |
| Example 7 | 600 | TiCl₃ aqueous solution | 3 g | AA | — | — | — | 37.70 | 4.34 | 6.93 | 5.44 | 240 |
| Example 8 | 600 | TiCl₃ aqueous solution | 7 g | AA | — | — | — | 49.31 | 4.78 | 7.44 | 6.63 | — |
| Example 9 | 600 | TiCl₃ aqueous solution × 2 | 5 g × 2 | AA | — | — | — | 5.69 | 1.52 | 21.68 | 0.26 | — |
| Example 10 | 600 | TiCl₃ aqueous solution | 1 g | AA | — | — | — | 30.40 | 4.21 | 13.18 | 2.31 | — |
| Comparative Example 1 | 120 | TiCl₄ | 50 ml | AA | — | — | — | 5.11 | 2.01 | 19.77 | 0.26 | — |
| Comparative Example 2 | 20 (air-drying) | TiCl₃ aqueous solution | 5 g | AA | — | — | — | 0.10 | 0.15 | 7.59 | 0.01 | — |
| Comparative Example 3 | 400 | TiCl₃ aqueous solution | 5 g | AA | — | — | — | 0.50 | 0.38 | 12.41 | 0.04 | — |
| Comparative Example 4 | 500 | TiCl₃ aqueous solution | 5 g | AA | — | — | — | 1.90 | 0.57 | 17.39 | 0.11 | — |
| Comparative Example 5 | 900 | TiCl₃ aqueous solution | 5 g | BB | — | — | — | — | — | — | — | — |
| Comparative Example 6 | — | gas-phase TiCl₄ | — | AA | 0.109 | 0.032 | 71.0 | 30.60 | 4.80 | 31.00 | 0.99 | 310 |
| Comparative Example 7 | — | Ti(OBu)₄ | — | AA | 0.118 | 0.076 | 138.0 | 3.40 | 1.10 | 48.00 | 0.07 | — |
| Reference Example | 600 | TiCl₃ aqueous solution | 1 g | AA | 0.030 | 0.360 | 31.8 | 0.70 | 0.08 | 8.80 | 0.08 | — |

(* in Table, the amount of titanium source added indicates an amount added per g of dealuminated UZM-35)

From Table 1, it is found that when primary calcination is carried out in the range of 550 to 850° C., preferably in the range of 600° C. to 800° C. before addition of a titanium source in a liquid phase, the yield of hydroquinone is improved and the selectivity of hydroquinone is enhanced.

(Physical Property Evaluations of Each Catalyst)

0.1 g of each catalyst obtained in the above Examples 1 to 4, Comparative Examples 6 and 7 and Reference Example was put in a cell, and analyzed in the range of 200 to 800 nm by using an ultraviolet visible analyzer (Shimadzu Corp., UV-2550) to measure absorbances at 210 nm and 300 nm. Further, the amounts of Si and Ti were measured by an ICP atomic emission spectrometer (Agilent Technologies, Inc., 720-ES) and the Si/Ti molar ratio was calculated. Results are shown in FIG. 1 and Table 1.

(Measuring Method)

In a 50 ml-internal volume flask equipped with a cooler, a thermometer, a feed pump and a magnetic stirrer chip, 0.2 g of each catalyst, 4.2 g of a phenol, 3.0 g of t-butyl alcohol and 6.0 g of water were placed and heated at 50° C. in a hot water bath with stirring by the stirrer. 0.5 g of a 34% hydrogen peroxide was added thereto dropwise from the feed pump over 10 min, and held as it was for 60 min. After the reaction liquid was cooled, the catalyst was filtered out, and a part of the reaction liquid was taken out and products were quantified by gas chromatography.

The analysis conditions of the gas chromatography were as follows.

Detector: a hydrogen flame ionization detector
Column: DB-5 (Agilent J&W), inner diameter: 0.25 mm, length: 60 m, membrane thickness: 0.25 μm
Column temperature: the temperature was held at 50° C. for 10 min and raised at a temperature-rise rate of 10° C./min up to 280° C.
Injection port: 280° C.
Detector temperature: 280° C.
Carrier gas: helium
Flow rate: 80 ml/min The specific surface area of a Ti-UZM-35 catalyst was measured by the BET method by using a nitrogen adsorption/desorption analyzer (manufactured by BEL Japan, Inc., BELSORP-max).

The present application claims priority based on Japanese Patent Application No. 2018-097032 and Japanese Patent Application No. 2018-097033, filed on May 21, 2018, and the contents described in the specification and claims of the applications are incorporated herein by reference.

The invention claimed is:

1. A method for manufacturing a modified aluminosilicate, comprising:
   a first step of treating an aluminosilicate with an acid;
   a second step of primarily calcining the treated material obtained in the first step at 550° C. to 850° C.;

a third step of contacting the calcined material obtained in the second step with a liquid containing one or more elements selected from the group consisting of Group 4 elements and Group 5 elements on the periodic table in a temperature range of 20 to 150° C. to obtain a material; and a fourth step of drying and secondarily calcining the material obtained in the third step, wherein a specific surface area of the modified aluminosilicate is 50 to 1000 m$^2$/g, and the modified aluminosilicate is zeolite having an MSE framework.

2. The method for manufacturing a modified aluminosilicate according to claim 1, wherein the liquid containing the elements is a liquid containing one or more elements selected from the group consisting of Group 4 elements.

3. The method for manufacturing a modified aluminosilicate according to claim 1, wherein the liquid containing the elements is a liquid containing titanium.

4. The method for manufacturing a modified aluminosilicate according to claim 3, wherein the liquid containing titanium is one or more selected from the group consisting of titanium tetrachloride, a titanium tetrachloride aqueous solution, a titanium trichloride aqueous solution and a titanium sulfate aqueous solution.

5. The method for manufacturing a modified aluminosilicate according to claim 1, wherein the zeolite having the MSE framework is one or more selected from the group consisting of UZM-35, MCM-68 and YNU-3.

6. A modified aluminosilicate, comprising one or more elements selected from the group consisting of Group 4 elements and Group 5 elements on the periodic table, and exhibiting an absorbance at 300 nm (A[300]) in an ultraviolet visible spectrum of 1.0 or higher, wherein a specific surface area of the modified aluminosilicate is 50 to 1000 m$^2$/g, and the modified aluminosilicate is zeolite having an MSE framework.

7. The modified aluminosilicate according to claim 6, wherein a ratio (A[300]/A[210]) of the absorbance at 300 nm (A[300]) in the ultraviolet visible spectrum to an absorbance at 210 nm (A[210]) in the ultraviolet visible spectrum is 0.5 or higher.

8. The modified aluminosilicate according to claim 6, wherein the element is one or more elements selected from Group 4 elements.

9. The modified aluminosilicate according to claim 6, wherein the element is titanium.

10. The modified aluminosilicate according to claim 9, wherein a molar ratio ([Si]/[Ti]) of silicon to titanium is in the range of 0.1 to 100.

11. A catalyst for manufacturing an aromatic dihydroxy compound, comprising the modified aluminosilicate according to claim.

12. A method for manufacturing an aromatic dihydroxy compound, comprising a step of reacting a phenol with hydrogen peroxide in the presence of the catalyst for manufacturing an aromatic dihydroxy compound according to claim 11.

* * * * *